United States Patent
Rytved et al.

(10) Patent No.: US 6,960,610 B2
(45) Date of Patent: Nov. 1, 2005

(54) USE OF GLYCOGEN PHOSPHORYLASE INHIBITORS FOR TREATMENT OF CARDIOVASCULAR DISEASES

(75) Inventors: Klaus Asger Rytved, Bagsvaerd (DK); Nils Dragsted, Stenlose (DK); Niels Chresten Berg Nyborg, Horsholm (DK); Lars Iversen, Hvidovre (DK); Marit Kristiansen, Soborg (DK)

(73) Assignee: Novo Nordick, A/S, Bagsvaerd (DK)

( * ) Notice: Subject to any disclaimer, the term of this patent is extended or adjusted under 35 U.S.C. 154(b) by 0 days.

(21) Appl. No.: 10/429,626

(22) Filed: May 5, 2003

(65) Prior Publication Data

US 2004/0082646 A1 Apr. 29, 2004

Related U.S. Application Data

(60) Provisional application No. 60/422,081, filed on Oct. 29, 2002.

(30) Foreign Application Priority Data

Oct. 28, 2002 (DK) .......................................... 2002 01630

(51) Int. Cl.⁷ ............................................... A61K 31/40
(52) U.S. Cl. ...................................... 514/408; 514/425
(58) Field of Search .................................. 514/408, 425

(56) References Cited

U.S. PATENT DOCUMENTS

| | | | |
|---|---|---|---|
| 5,998,463 A | 12/1999 | Hullin et al. | 514/418 |
| 6,277,877 B1 * | 8/2001 | Hoover et al. | 514/415 |
| 6,570,013 B2 * | 5/2003 | Mylari | 544/235 |

FOREIGN PATENT DOCUMENTS

| | | |
|---|---|---|
| AU | 2001 16399 A1 | 7/2001 |
| EP | 0846464 A2 | 12/1997 |
| EP | 1 125 580 A2 * | 8/2001 |
| WO | WO 95/24391 A1 | 9/1995 |
| WO | WO 96/39384 A1 | 12/1996 |
| WO | WO 97/09040 A1 | 3/1997 |
| WO | 00/47206 | 8/2000 |
| WO | WO 01/23347 A1 | 4/2001 |

OTHER PUBLICATIONS

Goodman and Gilman's The Pharmacological Basis of Therapeutics, $6^{th}$ ed., published 1980 (p. 749).*

Grundy, The New England Journal of Medicine, vol. 319, No. 1,(1988), pp 24–33.*

* cited by examiner

Primary Examiner—Raymond J. Henley, III
(74) Attorney, Agent, or Firm—Rosemarie R. Wilk-Orescan; Reza Green; Marc A. Began

(57) ABSTRACT

The present invention provides methods which may effectively be used in the treatment and prevention of early cardiac and early cardiovascular diseases, for example of ischemic origin, such as left ventricular hypertrophy, coronary artery disease, essential hypertension, acute hypertensive emergency, cardiomyopathy, heart insufficiency, exercise tolerance, chronic heart failure, arrhythmia, cardiac dysrhythmia, syncopy, arteriosclerosis, mild chronic heart failure, angina pectoris, cardiac bypass reocclusion, intermittent claudication (arteriosclerosis oblitterens), diastolic dysfunction and systolic dysfunction, as well as improving the success of heart transplantations, through administration of glycogen phosphorylase inhibitor compounds.

51 Claims, No Drawings

USE OF GLYCOGEN PHOSPHORYLASE INHIBITORS FOR TREATMENT OF CARDIOVASCULAR DISEASES

CROSS REFERENCE TO RELATED APPLICATIONS

This application claims priority under 35 U.S.C. 119 of Danish application PA 2002 01630, filed Oct. 28, 2002, and of U.S. Provisional application 60/422081 filed Oct. 29, 2002, the contents of which are fully incorporated herein by reference.

FIELD OF THE INVENTION

The present invention relates to methods for treatment and/or prevention of early cardiac and cardiovascular diseases, for instance of ischemic origin, by administration of a glycogen phosphorylase inhibitor.

BACKGROUND OF THE INVENTION

Cardiac and cardiovascular diseases, such as ventricular hypertrophy, coronary artery disease, essential hypertension, acute hypertensive emergency, cardiomyopathy, heart insufficiency, exercise tolerance, chronic heart failure, arrhythmia, cardiac dysrhythmia, syncopy, arteriosclerosis, mild chronic heart failure, angina pectoris, cardiac bypass reocclusion, intermittent claudication (arteriosclerosis obliterens), diastolic dysfunction and systolic dysfunction, are among the most common causes of death in the industrialized world.

During ischemia, the myocardial metabolism changes from utilisation of short chain free fatty acids and lactate under normoxic conditions to primarily breakdown of intracellular glycogen and anaerobic glycolysis causing net production of lactate and lowering of interstitial pH. The dramatic pH reduction within the myocardium following a total coronary artery occlusion causes profound changes in the cardiac electric conduction system and ion-channel function within the myocytes. These changes all in all lead to development of arrhythmia; particularly ventricular fibrillation which is in most cases fatal for the patient, unless acute intervention (defibrillation) and pharmacological treatment of the arrhythmia is initiated immediately after the onset. There is thus a pressing need for drugs which may help in reducing the mortality of such diseases.

Clinical accepted anti-arrhythmic agents exert their effect via interaction with ion channels in the myocardial conducting and/or contracting cells or by interference with beta-adrenoceptors. (2R, 3R, 4R)-3,4-dihydroxy-2-hydroxymethylpyrrolidine and related compounds are selective glycogen-phosphorylase inhibitors and are disclosed in WO97/09040 to Novo Nordisk A/S for the treatment of type 2 diabetes. WO 95/24391 and WO01/23347 to Novo Nordisk A/S discloses other groups of glycogen-phosphorylase inhibitors, which may be used for the treatment of type 2 diabetes. These compounds have not been associated with interference with the electric conduction system of the heart and are as such not associated with arrhythmic potential or other cardiovascular effects as the other known anti-arrhythmic agents used in clinical therapy today, such as lidocaine, amiodarone, sotalol and others Class I–IV anti-arrhythmic drugs.

WO96/39384 to Pfizer, Inc. concerns the use of a class of glycogen phosphorylase inhibitors for treating hyperglycaemia, diabetes, hypercholesterolaemia, atherosclerosis, hyperinsulinaemia, hypertension, hyperlipidaemia and myocardial ischemia.

Patent application EP 1125580 to Pfizer, Inc. concerns methods of treating specifically diabetic cardiomyopathy comprising administration of a therapeutically effective amount of a glycogen phosphorylase inhibitor to a patient having or at risk of having diabetic cardiomyopathy.

Patent application EP0846464 to Pfizer, Inc. concerns the use of a glycogen phosphorylase inhibitor for the manufacture of a medicament for reducing non-cardiac tissue damage resulting from ischemia or hypoxia.

SUMMARY OF THE INVENTION

One object of the present invention is to provide compounds which may effectively be used in the treatment and prevention of early cardiac and early cardiovascular diseases, for instance of ischemic origin, such as left ventricular hypertrophy, coronary artery disease, essential hypertension, acute hypertensive emergency, cardiomyopathy, heart insufficiency, exercise tolerance, chronic heart failure, arrhythmia, cardiac dysrhythmia, syncopy, arteriosclerosis, mild chronic heart failure, angina pectoris, cardiac bypass reocclusion, intermittent claudication (arteriosclerosis oblitterens), diastolic dysfunction and systolic dysfunction.

Another object of the present invention is to provide compounds which may effectively be used in improving the success of heart transplantations.

In one embodiment, the present invention provides a method for treatment of an early cardiac or early cardiovascular disease, the method comprising administering to a subject in need thereof an effective amount of a compound of the general formula (I)

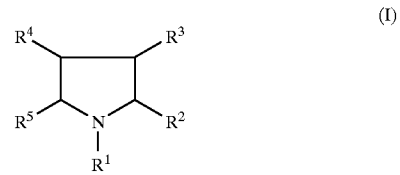

(I)

wherein
$R^1$ is hydrogen or acyl, alkenyl, cycloalkyl or alkyl, all of which are optionally substituted with one or more of the following groups: hydroxy, alkoxy, amino, N-alkylamino, N,N-dialkylamino, halogen, cycloalkyl, optionally substituted phenyl or alkoxycarbonyl;
$R^2$ is hydrogen or alkyl;
$R^3$ and $R^4$, which are the same or different, independent of each other, is hydrogen, halogen, hydroxy, mercapto or amino which is optionally substituted with alkyl or aralkyl; and
$R^5$ is alkyl substituted with hydroxy, halogen, amino, N-alkylamino, N,N-dialkylamino or mercapto;
or a pharmaceutically acceptable salt or hydrate or prodrug thereof including any of the optical or geometric isomers or tautomeric forms or mixtures thereof.

Further embodiments of the invention are clear from the appended claims.

Definitions

In the above structural formulas and throughout the present specification, the following terms have the indicated meaning:

"Halogen" designates an atom selected from the group consisting of F, Cl, Br or I.

The use of prefixes of this structure: $C_{x-y}$-alkyl, $C_{x-y}$-alkenyl, $C_{x-y}$-alkynyl, $C_{x-y}$-cycloalkyl or $C_{x-y}$-cycloalkyl- $C_{x-y}$-alkenyl-designates radical of the designated type having from x to y carbon atoms.

The term "alkyl" as used herein, alone or in combination, refers to a straight or branched chain saturated monovalent hydrocarbon radical having for instance from one to ten carbon atoms, for example $C_{1-8}$-alkyl. Typical $C_{1-8}$-alkyl groups include, but are not limited to e.g. methyl, ethyl, n-propyl, isopropyl, n-butyl, sec-butyl, isobutyl, tert-butyl, n-pentyl, 2-methylbutyl, 3-methylbutyl, 4-methylpentyl, neopentyl, n-pentyl, n-hexyl, 1,2-dimethylpropyl, 2,2-dimethylpropyl, 1,2,2-trimethylpropyl and the like. The term "$C_{1-8}$-alkyl" as used herein also includes secondary $C_{3-8}$-alkyl and tertiary $C_{4-8}$-alkyl.

The term "alkenyl" as used herein, alone or in combination, refers to a straight or branched chain monovalent hydrocarbon radical having for instance from two to ten carbon atoms and at least one carbon-carbon double bond, for example $C_{2-8}$-alkenyl. Typical $C_{2-8}$-alkenyl groups include, but are not limited to, vinyl, 1-propenyl, 2-propenyl, iso-propenyl, 1,3-butadienyl, 1-butenyl, 2-butenyl, 3-butenyl, 2-methyl-1-propenyl, 1-pentenyl, 2-pentenyl, 3-pentenyl, 4-pentenyl, 3-methyl-2-butenyl, 1-hexenyl, 2-hexenyl, 3-hexenyl, 2,4-hexadienyl, 5-hexenyl and the like.

The term "cycloalkyl" as used herein, alone or in combination, refers to a non-aromatic monovalent hydrocarbon radical having for instance from three to twelve carbon atoms, and optionally with one or more degrees of unsaturation, for example $C_{3-8}$-cycloalkyl. Such a ring may be optionally fused to one or more benzene rings or to one or more of other cycloalkyl ring(s). Typical $C_{3-8}$-cycloalkyl groups include, but are not limited to, cyclopropyl, cyclobutyl, cyclopentyl, cyclohexyl, cyclohexenyl, cycloheptyl, cycloheptenyl, cyclooctyl and the like.

The term "alkoxy" as used herein, alone or in combination, refers to the monovalent radical $R^aO$—, where $R^a$ is alkyl as defined above, for example $C_{1-8}$-alkyl giving $C_{1-8}$-alkoxy. Typical $C_{1-8}$-alkoxy groups include, but are not limited to, methoxy, ethoxy, n-propoxy, isopropoxy, butoxy, sec-butoxy, tert-butoxy, pentoxy, isopentoxy, hexoxy, iso-hexoxy and the like.

The term "alkoxycarbonyl" as used herein refers to the monovalent radical $R^aOC(O)$—, where $R^a$ is alkyl as described above, for example $C_{1-8}$-alkoxycarbonyl. Typical $C_{1-8}$-alkoxycarbonyl groups include, but are not limited to, methoxycarbonyl, ethoxycarbonyl, propoxycarbonyl, isopropoxycarbonyl, n-butoxycarbonyl, sec-butoxycarbonyl, tertbutoxycarbonyl, 3-methylbutoxycarbonyl, n-hexoxycarbonyl and the like.

The term "mercapto" as used herein refers to the substituent HS—.

The term "acyl" as used herein refers to a group of the formula $R^a$—C(O)—, wherein $R^a$ is hydrogen, alkyl or aryl.

In the present context, the terms N-alkylamino and N,N-dialkylamino are intended to indicate radicals of the formula —NHR' and —NR'R', respectively, wherein each R' independently represents alkyl as indicated above.

The term "optionally substituted" as used herein means that the groups in question are either unsubstituted or substituted with one or more of the substituents specified. When the groups in question are substituted with more than one substituent, the substituents may be the same or different.

The terms "treatment" and "treating" as used herein mean the management and care of a patient for the purpose of combating a condition, such as a disease or a disorder. The term is intended to include the full spectrum of treatments for a given condition from which the patient is suffering, such as administration of the active compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of a patient for the purpose of combating the disease, condition, or disorder and includes the administration of the active compounds to prevent the onset of the symptoms or complications. The patient to be treated is preferably a mammal, in particular a human being.

Within the context of the present invention, a "glycogen phosphorylase inhibitor" is understood to refer to any compound, including peptides and non-peptide compounds, which fully or partially inhibits the glycogen phosphorylase enzyme.

DETAILED DESCRIPTION OF INVENTION

The synthesis of compounds of the general formula (I) is described in WO97/09040 to Novo Nordisk A/S, which is hereby incorporated by reference.

In one embodiment, the compound of formula (I) contains at least two or at least three hydroxy groups.

In one embodiment, the compound of formula (I) has a structure wherein the two substituents designated by the symbols $R^3$ and $R^5$ are situated at the same side of the plane formed by the five membered nitrogen containing ring, and $R^4$ is situated at the opposite side of the plane formed by the five membered nitrogen containing ring.

In one embodiment, $R^1$ is hydrogen, acyl or alkyl which is optionally substituted with one or more of the following groups: hydroxy, alkoxy, amino, N-alkylamino, N,N-dialkylamino, phenyl or alkoxycarbonyl. Particularly in this embodiment, $R^1$ may represent optionally substituted $C_{1-6}$alkyl, such as optionally substituted methyl.

In one embodiment, $R^1$ is substituted with an phenyl group, optionally substituted with one or more substituents selected from the group consisting of halogen, hydroxy, alkoxy, trifluoroalkyl and cyano.

In one embodiment, $R^2$ represents hydrogen or $C_{1-6}$-alkyl, such as methyl.

In one embodiment, $R^3$ represents hydrogen, hydroxy, halogen, e.g. flouro, or amino.

In one embodiment, $R^4$ represents hydrogen, hydroxy, halogen, e.g. flouro, or amino.

In one embodiment, $R^5$ represents hydroxyalkyl, such as $C_{1-6}$hydroxyalkyl, such as hydroxymethyl, hydroxyethyl or hydroxypropyl.

In one embodiment, $R^5$ represents benzyloxymethyl.

Examples of compounds of formula (I) for use according to the present invention are
3,4-dihydroxy-2-hydroxymethylpyrrolidine,
3-4-dihydroxy-2-hydroxymethyl-1-methylpyrrolidine,
1-cyclopropylmethyl-3,4-dihydroxy-2-hydroxymethylpyrrolidine,
3,4-dihydroxy-2-hydroxymethyl-1-propylpyrrolidine,
1-butyl-3,4-dihydroxy-2-hydroxymethylpyrrolidine,
3,4-dihydroxy-2-hydroxymethyl-1-(2,2,2-trifluoroethyl)-pyrrolidine,
1-benzyl-3,4-dihydroxyy-2-hydroxymethylpyrrolidine,
3,4-dihydroxy-2-hydroxymethyl-1-(2-hydroxyethyl) pyrrolidine,
3,4-dihydroxy-2-hydroxymethyl-1-(1,3-dihydroxyprop-2-yl)pyrrolidine, 3,4-dihydroxy-2-hydroxymethyl-1-(2,3-dihydroxyprop-1-yl)pyrrolidine,
1-(2-aminoethyl)-3,4-dihydroxy-2-hydroxymethylpyrrolidine,
or any of the optical isomers thereof.

Specific examples of compounds of formula (I) for use according to the present invention are
(2R,3R,4R)-3,4dihydroxy-2-hydroxymethylpyrrolidine,
(2R,3R,4R)-3,4-dihydroxy-2-hydroxymethyl-1-methylpyrrolidine,
(2R,3R,4R)-1-cyclopropylmethyl-3,4-dihydroxy-2-hydroxymethylpyrrolidine,
(2R,3R,4R)-3,4-dihydroxy-2-hydroxymethyl-1-propylpyrrolidine,
(2R,3R,4R)-1-butyl-3,4dihydroxy-2-hydroxymethylpyrrolidine,
(2R,3R,4R)-3,4-dihydroxy-2-hydroxymethyl-1-(2,2,2-trifluoroethyl)pyrrolidine,
(2R,3R,4R)-1-benzyl-3,4-dihydroxy-2-hydroxymethylpyrrolidine,
(2R,3R,4R)-3,4-dihydroxy-2-hydroxymethyl-1-(2-hydroxyethyl)pyrrolidine,
(2R,3R,4R)-3,4-dihydroxy-2-hydroxymethyl-1-(2,3-dihydroxyprop-1-yl)pyrrolidine,
(2R,3R,4R)-3,4-dihydroxy-2-hydroxymethyl-1-(1,3-dihydroxyprop-2-yl)pyrrolidine,
(2R,3R,4R)-1-(2-aminoethyl)-3,4-dihydroxy-2-hydroxymethylpyrrolidine,
(2S,3S,4S)-3,4-dihydroxy-2-hydroxymethylpyrrolidine,
(2S,3S,4S)-3,4-dihydroxy-2-hydroxymethyl-1-methylpyrrolidine,
(2S,3S,4S)-1-cyclopropylmethyl-3,4-dihydroxy-2-hydroxymethylpyrrolidine,
(2S,3S,4S)-3,4-dihydroxy-2-hydroxymethyl-1-propylpyrrolidine,
(2S,3S,4S)-1-butyl-3,4-dihydroxy-2-hydroxymethylpyrrolidine,
(2S,3S,4S)-3,4-dihydroxy-2-hydroxymethyl-1-(2,2,2-trifluoroethyl)pyrrolidine,
(2S,3S,4S)-1-benzyl-3,4-dihydroxy-2-hydroxymethylpyrrolidine,
(2S,3S,4S)-3,4-dihydroxy-2-hydroxymethyl-1-(2-hydroxyethyl)pyrrolidine,
(2S,3S,4S)-3,4-dihydroxy-2-hydroxymethyl-1-(2,3-dihydroxyprop-1-yl)pyrrolidine,
(2S,3S,4S)-3,4-dihydroxy-2-hydroxymethyl-1-(1,3-dihydroxyprop-2-yl)-pyrrolidine, or
(2S,3S,4S)-1-(2-aminoethyl)-3,4-dihydroxy-2-hydroxymethyl-pyrrolidine.

Compounds of the general formula (I) cause a significant reduction in time with ischemia induced arrhythmia. The potential of these compounds to inhibit ischemia-induced arrhythmia is associated with a very large cardiovascular safety margin which is advantageous and in sharp contrast to the clinically used ion-channel/beta-adrenoceptor interfering anti-arrhythmic agents. A chronic therapy of patients at risk will be potentially safer with these compounds than with conventional therapy.

Compounds of general formula (I) also cause a significant reduction of the size of ischemia induced infarct, and the compounds therefore have cardioprotective effects.

Compounds of general formula I also reduce the amount of glycogen metabolised in the heart tissue during ischemia, which endows compounds of formula (I) with cardioprotective effects.

Furthermore, compounds of the general formula (I) do not affect glucose uptake in muscle cells and have an attractive toxicity profile. It is believed to be a particular advantage of the methods of the present invention that the compounds of formula I do not affect the glucose uptake in muscles because this would lead to fatigue and tiredness with the patient. For patients, and in particular for patients in chronic or long-lasting treatment, fatigue and tiredness would be an adverse effect which severely reduces the quality of life. That compounds of formula I do not affect glucose uptake in muscles enables the use of said compounds with fewer adverse effects in general, and in chronic or long-lasting treatment in particular.

Thus, compounds of the general formula (I) are potential drugs for the treatment and prevention of a wide range of cardiac and cardiovascular diseases, for instance of ischemic origin, as well as for use in connection with heart transplants, where the endpoints will be increased survival of the hearts, less waste, better pump function after implantation and a decreased frequency of heart pump failure and multi organ failure.

Accordingly, the present invention is directed to the use of a glycogen phosphorylase inhibitor, such as a compound of general formula (I) or a pharmaceutically acceptable salt thereof for the preparation of a pharmaceutical composition for the treatment or prevention of an early cardiac or early cardiovascular disease in a subject in need thereof. By an early cardiac or early cardiovascular disease is meant a stage of disease prior to stroke or myocardial infarct.

The present invention is also directed to the use of a glycogen phosphorylase inhibitor, such as a compound of general formula (I), or a pharmaceutically acceptable salt thereof for the preparation of a pharmaceutical composition for use in connection with heart transplantations in a subject in need thereof.

The present invention also provides methods for the treatment of an early cardiac or early cardiovascular disease, the method comprising administering to a subject in need thereof a therapeutically effective amount of a compound of formula (I).

In one embodiment the early cardiac or early cardiovascular disease is selected from the group consisting of left ventricular hypertrophy, coronary artery disease, essential hypertension, acute hypertensive emergency, cardiomyopathy, heart insufficiency, exercise tolerance, chronic heart failure, arrhythmia, cardiac dysrhythmia, syncopy, arteriosclerosis, mild chronic heart failure, angina pectoris, cardiac bypass reocclusion, intermittent claudication (arteriosclerosis oblitterens), diastolic dysfunction and systolic dysfunction.

In one embodiment the early cardiac or early cardiovascular disease is arrhythmia.

In one embodiment the subject suffers from a disease selected from the group consisting of left ventricular hypertrophy, coronary artery disease, essential hypertension, acute hypertensive emergency, cardiomyopathy, heart insufficiency, exercise tolerance, chronic heart failure, arrhythmia, cardiac dysrhythmia, syncopy, arteriosclerosis, mild chronic heart failure, angina pectoris, cardiac bypass reocclusion, intermittent claudication (arteriosclerosis oblitterens), diastolic dysfunction and systolic dysfunction.

In one embodiment the subject is at risk of contracting a disease selected from the group consisting of left ventricular hypertrophy, coronary artery disease, essential hypertension, acute hypertensive emergency, cardiomyopathy, heart insufficiency, exercise tolerance, chronic heart failure, arrhythmia, cardiac dysrhythmia, syncopy, arteriosclerosis, mild chronic heart failure, angina pectoris, cardiac bypass reocclusion, intermittent claudication (arteriosclerosis oblitterens), diastolic dysfunction and systolic dysfunction.

In one embodiment the patient suffers from a disease selected from the group consisting of myocardial infarct, acute coronary syndrome, unstable angina, non-Q-wave cardiac necrosis, Q-wave myocardial infarct and morbidity after stroke.

In one embodiment the patient is at risk of contracting a disease selected from the group consisting of myocardial infarct, acute coronary syndrome, unstable angina, non-Q-wave cardiac necrosis, Q-wave myocardial infarct and morbidity after stroke.

In one embodiment, the patient is a non-diabetic patient.

In one embodiment, the invention provides a method for reducing the size of an ischemia induced heart infract or for reducing the ischemia induced increase in glycogen metabolism in heart tissue, the method comprising administering to a subject in need thereof an effective amount of a compound of formula (I).

In one embodiment, the invention provides a method for increasing survival of transplanted hearts, improving pump function of transplanted hearts, decreasing the frequency of pump failure in transplanted hearts or for reducing the frequency of multi organ failure in connection with hearts transplantations, the method comprising administering to a patient with a transplanted heart or about to have a heart transplanted an effective amount of a compound of the general formula (I).

In one embodiment, the treatment is in combination with one or more further pharmaceutical agents.

In a further embodiment, said further pharmaceutical agent is selected from the group consisting of anti-arrhythmia agents, anti-diabetic agents, anti-obesity agents, lipid modulating agents, anti-hypertensive agents and anti-osteoporosis agents.

In one embodiment, the anti-arrhythmia agent is digoxin.

In one embodiment, the anti-diabetic agent is metformin.

In one embodiment, the anti-hypertensive agent is an angiotensin converting enzyme inhibitor.

In one embodiment, the angiotensin converting enzyme inhibitor is selected from the group consisting of captopril, enalapril, fosinoprol, lisnoprol, quinapril, ramipril and spirapril.

In one embodiment, the anti-hypertensive agent is an angiotensin II receptor antagonist, e.g. losartan.

In one embodiment, the anti-hypertensive agent is a non-subtype-selective β-adrenergic antagonist.

In one embodiment, the non-subtype-selective β-adrenergic antagonist is selected from the group consisting of propranolol, nadolol, timolol and pindolol.

In one embodiment, the antihypertensive agent is a selective $β_1$-adrenergic antagonist.

In one embodiment, the selective $β_1$-adrenergic antagonist is selected from the group consisting of metoprolol, atenolol, esmolol and acebutolol.

The present invention also encompasses pharmaceutically acceptable salts of the glycogen phosphorylase inhibitors, such as of a compound of general formula (I). Such salts include pharmaceutically acceptable acid addition salts, pharmaceutically acceptable metal salts, ammonium salts and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids and the like. Further examples of pharmaceutically acceptable inorganic or organic acid addition salts include the pharmaceutically acceptable salts listed in J. Pharm. Sci. 1977, 66, 2. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like.

The present invention also encompasses prodrugs of a compound according to the invention which on administration undergo chemical conversion by metabolic processes before becoming active pharmacological substances. In general, such prodrugs will be functional derivatives of a compound of the invention which are readily convertible in vivo into a compound of the invention. Conventional procedures for the selection and preparation of suitable prodrug derivatives are described, for example, in "Design of Prodrugs", ed. H. Bundgaard, Elsevier, 1985.

The ester derivatives of formula (I) could be suitable prodrugs.

The route of administration may be any route, which effectively transports the active compound to the appropriate or desired site of action, such as oral, nasal, buccal, pulmonal, transdermal or parenteral.

Pharmaceutical Compositions

The compounds for use according to the present invention may be administered alone or in combination with pharmaceutically acceptable carriers or excipients, in either single or multiple doses. The pharmaceutical compositions according to the present invention may be formulated with pharmaceutically acceptable carriers or diluents as well as any other known adjuvants and excipients in accordance with conventional techniques such as those disclosed in Remington: The Science and Practice of Pharmacy, $19^{th}$ Edition, Gennaro, Ed., Mack Publishing Co., Easton, Pa., 1995.

The pharmaceutical compositions may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the oral route being preferred. It will be appreciated that the preferred route will depend on the general condition and age of the subject to be treated, the nature of the condition to be treated and the active ingredient chosen.

Pharmaceutical compositions for oral administration include solid dosage forms such as hard or soft capsules, tablets, troches, dragees, pills, lozenges, powders and granules. Where appropriate, they can be prepared with coatings such as enteric coatings or they can be formulated so as to provide controlled release of the active ingredient such as sustained or prolonged release according to methods well known in the art.

Liquid dosage forms for oral administration include solutions, emulsions, aqueous or oily suspensions, syrups and elixirs.

Pharmaceutical compositions for parenteral administration include sterile aqueous and non-aqueous injectable solutions, dispersions, suspensions or emulsions as well as sterile powders to be reconstituted in sterile injectable solutions or dispersions prior to use. Depot injectable formulations are also contemplated as being within the scope of the present invention.

Other suitable administration forms include suppositories, sprays, ointments, creams, gels, inhalants, dermal patches, implants, etc.

A typical oral dosage is in the range of from about 0.001 to about 100 mg/kg body weight per day, preferably from about 0.01 to about 50 mg/kg body weight per day, and more preferred from about 0.05 to about 10 mg/kg body weight per day administered in one or more dosages such as 1 to 3 dosages. The exact dosage will depend upon the frequency and mode of administration, the sex, age, weight and general condition of the subject treated, the nature and severity of the condition treated and any concomitant diseases to be treated and other factors evident to those skilled in the art.

The formulations may conveniently be presented in unit dosage form by methods known to those skilled in the art. A typical unit dosage form for oral administration one or more times per day such as 1 to 3 times per day may contain from 0.05 to about 1000 mg, preferably from about 0.1 to about 500 mg, and more preferred from about 0.5 mg to about 200 mg.

For parenteral routes such as intravenous, intrathecal, intramuscular and similar administration, typically doses are in the order of about half the dose employed for oral administration.

The compounds for use according to the present invention are generally utilized as the free substance or as a pharmaceutically acceptable salt thereof. Examples are an acid addition salt of a compound having the utility of a free base and a base addition salt of a compound having the utility of a free acid. The term "pharmaceutically acceptable salts" refers to non-toxic salts of the compounds for use according to the present invention which are generally prepared by reacting the free base with a suitable organic or inorganic acid or by reacting the acid with a suitable organic or inorganic base. When a compound for use according to the present invention, such as a compound of Formula (I) contains a free base such salts are prepared in a conventional manner by treating a solution or suspension of the compound with a chemical equivalent of a pharmaceutically acceptable acid. When a compounds for use according to the present invention, such as a compound of Formula (II), contains a free acid such salts are prepared in a conventional manner by treating a solution or suspension of the compound with a chemical equivalent of a pharmaceutically acceptable base. Physiologically acceptable salts of a compound with a hydroxy group include the anion of said compound in combination with a suitable cation such as sodium or ammonium ion. Other salts which are not pharmaceutically acceptable may be useful in the preparation of compounds for use according to the present invention and these form a further aspect of the present invention.

For parenteral administration, solutions of the compounds for use according to the present invention in sterile aqueous solution, aqueous propylene glycol or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Suitable pharmaceutical carriers include inert solid diluents or fillers, sterile aqueous solution and various organic solvents. Examples of solid carriers are lactose, terra alba, sucrose, cyclodextrin, talc, gelatine, agar, pectin, acacia, magnesium stearate, stearic acid and lower alkyl ethers of cellulose. Examples of liquid carriers are syrup, peanut oil, olive oil, phospholipids, fatty acids, fatty acid amines, polyoxyethylene and water. Similarly, the carrier or diluent may include any sustained release material known in the art, such as glyceryl monostearate or glyceryl distearate, alone or mixed with a wax. The pharmaceutical compositions formed by combining the compounds for use according to the present invention and the pharmaceutically acceptable carriers are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units such as capsules or tablets, each containing a predetermined amount of the active ingredient, and which may include a suitable excipient. Furthermore, the orally available formulations may be in the form of a powder or granules, a solution or suspension in an aqueous or non-aqueous liquid, or an oil-in-water or water-in-oil liquid emulsion.

Compositions intended for oral use may be prepared according to any known method, and such compositions may contain one or more agents selected from the group consisting of sweetening agents, flavouring agents, colouring agents, and preserving agents in order to provide pharmaceutically elegant and palatable preparations. Tablets may contain the active ingredient in admixture with non-toxic pharmaceutically-acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch or alginic acid; binding agents, for example, starch, gelatine or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,356,108; 4,166,452; and 4,265,874, incorporated herein by reference, to form osmotic therapeutic tablets for controlled release.

Formulations for oral use may also be presented as hard gelatine capsules where the active ingredient is mixed with an inert solid diluent, for example, calcium carbonate, calcium phosphate or kaolin, or a soft gelatine capsule wherein the active ingredient is mixed with water or an oil medium, for example peanut oil, liquid paraffin, or olive oil.

Aqueous suspensions may contain the active compounds in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide such as lecithin, or condensation products of an alkylene oxide with fatty acids, for example polyoxyethylene stearate, or condensation products of ethylene oxide with long chain aliphatic alcohols, for example, heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more colouring agents, one or more flavouring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as a liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example, sweetening, flavouring, and colouring agents may also be present.

The pharmaceutical compositions comprising a compound for use according to the present invention may also be in the form of oil-in-water emulsions. The oily phase may be a vegetable oil, for example, olive oil or arachis oil, or a mineral oil, for example a liquid paraffin, or a mixture thereof. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative, and flavouring and colouring agents. The pharmaceutical compositions may be in the form of a sterile injectable aqueous or oleaginous suspension. This suspension may be formulated according to the known methods using suitable dispersing or wetting agents and suspending agents described above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution, and isotonic sodium chloride solution. In addition, sterile, fixed oils are conveniently employed as solvent or suspending medium. For this purpose, any bland fixed oil may be employed using synthetic mono- or diglycerides. In addition, fatty acids such as oleic acid find use in the preparation of injectables.

The compositions may also be in the form of suppositories for rectal administration of the compounds of the present invention. These compositions can be prepared by mixing the drug with a suitable non-irritating excipient which is solid at ordinary temperatures but liquid at the rectal temperature and will thus melt in the rectum to release the drug. Such materials include cocoa butter and polyethylene glycols, for example.

For topical use, creams, ointments, jellies, solutions or suspensions, etc., containing the compounds of the present invention are contemplated. For the purpose of this application, topical applications shall include mouth washes and gargles.

The compounds for use according to the present invention may also be administered in the form of liposome delivery systems, such as small unilamellar vesicles, large unilamellar vesicles, and multilamellar vesicles. Liposomes may be formed from a variety of phospholipids, such as cholesterol, stearylamine, or phosphatidylcholines.

In addition, some of the compounds for use according to the present invention may form solvates with water or common organic solvents. Such solvates are also encompassed within the scope of the present invention.

Thus, in a further embodiment, there is provided a pharmaceutical composition comprising a compound for use according to the present invention, or a pharmaceutically acceptable salt, solvate, or prodrug thereof, and one or more pharmaceutically acceptable carriers, excipients, or diluents.

If a solid carrier is used for oral administration, the preparation may be tabletted, placed in a hard gelatine capsule in powder or pellet form or it can be in the form of a troche or lozenge. The amount of solid carrier will vary widely but will usually be from about 25 mg to about 1 g. If a liquid carrier is used, the preparation may be in the form of a syrup, emulsion, soft gelatine capsule or sterile injectable liquid such as an aqueous or non-aqueous liquid suspension or solution.

A typical tablet that may be prepared by conventional tabletting techniques may contain:

| Core: | |
|---|---|
| Active compound ((2R,3R,4R)-3,4dihydroxy-2-hydroxymethylpyrrolidine, free compound or salt thereof) | 5.0 mg |
| Lactosum Ph. Eur. | 67.8 mg |
| Cellulose, microcryst. (Avicel) | 31.4 mg |
| Amberlite ®IRP88* | 1.0 mg |
| Magnesii stearas Ph. Eur. | q.s. |
| Coating: | |
| Hydroxypropyl methylcellulose | approx. 9 mg |
| Mywacett 9–40 T** | approx. 0.9 mg |

*Polacrillin potassium NF, tablet disintegrant, Rohm and Haas.
**Acylated monoglyceride used as plasticizer for film coating.

If desired, the pharmaceutical composition for use according to the present invention may comprise a compound for use according to the present invention in combination with further active substances such as those described in the foregoing.

The pharmaceutical composition may be administered continuously by infusion, one or more times daily such as one to three times daily or at longer intervals such as weekly or monthly in the form of a depot preparation.

In one embodiment the pharmaceutical composition is administered to the patient acutely or for instance for more than 1 week, such as for more than 4 weeks, for instance for more than 3 months, such as for more than 6 months.

In another aspect the present invention relates to the use of a glycogen phosphorylase inhibitor, such as a compound of general formula (I), wherein one or more further pharmaceutical agents are administered to the patient. These further pharmaceutical agents may be administered simultaneously, separately or sequentially with the glycogen phosphorylase inhibitor.

In one embodiment said further pharmaceutical agent is selected from the group consisting of anti-arrhythmia agents, anti-diabetic agents, anti-obesity agents, lipid modulating agents, anti-hypertensive agents and antiosteoporosis agents.

Relevant ant diabetic agents include insulin, metformin, insulin analogues and derivatives such as those disclosed in EP 0 792 290 (Novo Nordisk A/S), eg $N^{\epsilon B29}$-tetradecanoyl des (B30) human insulin, EP 0 214 826 and EP 0 705 275 (Novo Nordisk A/S), eg $Asp^{B28}$ human insulin, U.S. Pat. No. 5,504,188 (Eli Lilly), eg $Lys^{B28}$ $Pro^{B29}$ human insulin, and EP 0 368 187 (Aventis), eg Lantus®.

Anti-arrhythmia agents are often classified into four main groups according to their mechanism of action: sodium channel blockade, beta-adrenergic blockade, repolarization prolongation, or calcium channel blockade. The most common one is digoxin, but also adenosine, amiodarone hydrochloride, aprindine, atenolol, atropine sulfate, carteolol hydrochloride, celiprolol hcl, disopyramide, edrophonium chloride, felodipine, fendiline hcl, lidocaine hydrochloride, losartan potassium, metipranolol, metoprolol, metoprolol fumarate, metoprolol tartrate, mexiletine hydrochloride, nicorandil, oxprenolol hydrochloride, phenytoin, pindolol, procainamide hydrochloride, propafenone hydrochloride, propranolol hydrochloride, quinidine bisulfate, sotalol hydrochloride, timolol, timolol maleate, and verapamil hydrochloride are contemplated for use in combination with a compound of general formula (I) as described above.

The orally active hypoglycaemic agents preferably comprise imidazolines, sulfonylureas, biguanides, such as metformin, meglitinides, oxadiazolidinediones, thiazolidinediones, insulin sensitizers, α-glucosidase inhibitors, agents acting on the ATP-dependent potassium channel of the β-cells eg potassium channel openers such as those disclosed in WO 97/26265, WO 99/03861 and WO 00/37474 (Novo Nordisk A/S), or mitiglinide, or a potassium channel blocker, such as BTS-67582, nateglinide, glucagon antagonists such as those disclosed in WO 99/01423 and WO 00/39088 (Novo Nordisk A/S and Agouron Pharmaceuticals, Inc.), GLP-1 agonists such as those disclosed in WO 00/42026 (Novo Nordisk A/S and Agouron Pharmaceuticals, Inc.), DPP-IV (dipeptidyl peptidase-IV) inhibitors, PTPase (protein tyrosine phosphatase) inhibitors, inhibitors of hepatic enzymes involved in stimulation of gluconeogenesis and/or glycogenolysis, glucose uptake modulators, GSK-3 (glycogen synthase kinase-3) inhibitors, compounds modifying the lipid metabolism such as antilipidemic agents, compounds lowering food intake, PPAR (peroxisome proliferator-activated receptor) and R×R (retinoid×receptor) agonists, such as ALRT-268, LG-1268 or LG-1069.

Relevant anti-obesity agents include CART (cocaine amphetamine regulated transcript) agonists, NPY (neuropeptide Y) antagonists, MC4 (melanocortin 4) agonists, MC3 (melanocortin 3) agonists, orexin antagonists, TNF (tumor necrosis factor) agonists, CRF (corticotropin releasing factor) agonists, CRF BP (corticotropin releasing factor binding protein) antagonists, urocortin agonists, β3 adrenergic agonists such as CL-316243, AJ-9677, GW-0604, LY362884, LY377267 or AZ-40140, MSH (melanocyte-stimulating hormone) agonists, MCH (melanocyte-concentrating hormone) antagonists, CCK (cholecystokinin) agonists, serotonin re-uptake inhibitors such as fluoxetine, seroxat or citalopram, serotonin and noradrenaline re-uptake inhibitors, mixed serotonin and noradrenergic compounds, 5HT (serotonin) agonists, bombesin agonists, galanin antagonists, growth hormone, growth factors such as prolactin or placental lactogen, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, PPAR (peroxisome proliferator-activated receptor) modulators, R×R (retinoid×receptor) modulators, TR β agonists, AGRP (Agouti related protein) inhibitors, opioid antagonists (such as naltrexone), H3 histamine antagonists and ciliary neurotrophic factor.

Relevant lipid modulating agents include cholestyramine, colestipol, clofibrate, gemfibrozil, lovastatin, pravastatin, simvastatin, probucol and dextrothyroxine.

In one embodiment the anti-hypertensive agent is an angiotensin converting enzyme inhibitor.

In one embodiment the angiotensin converting enzyme inhibitor is selected from the group consisting of captopril, enalapril, fosinoprol, lisnoprol, quinapril, ramipril and spirapril.

In one embodiment the anti-hypertensive agent is an angiotensin II receptor antagonist, e.g. losartan.

In one embodiment the anti-hypertensive agent is a non-subtype-selective β-adrenergic antagonist.

In one embodiment the non-subtype-selective β-adrenergic antagonist is selected from the group consisting of propranolol, nadolol, timolol and pindolol.

In one embodiment the antihypertensive agent is a selective $β_1$-adrenergic antagonist.

In one embodiment the selective $β_1$-adrenergic antagonist is selected from the group consisting of metoprolol, atenolol, esmolol and acebutolol.

EXAMPLES

Example 1

Functional Characterisation of Glycogen Phosphorylase Inhibitors

Fosgerau et al, Kinetic and functional characterization of 1,4-dideoxy-1,4-imino-D-arabinitol. A potent inhibitor of glycogen phosphorylase with anti-hyperglyceamic effect in ob/ob mice, Archives of Biochemistry and Biophysics 380, 274–284 (2000), which is hereby incorporated in its entirety by reference, describes assays for determination of whether a given compound is a glycogen phosphorylase inhibitor.

Results:

Rabbit and rat heart glycogen phosphorylase was inhibited by (2R,3R,4R)-3,4dihydroxy-2-hydroxymethylpyrrolidin with an IC50 of 220 nM in the direction of glycogen breakdown.

Example 2

Effect on Ischemia Induced Arrhythmia in the Isolated Perfused Rabbit Heart

The model evaluates the effect of a test compound on ischemia induced arrhythmia in isolated perfused rabbit hearts.

Method:

The hearts were excised from rabbits and perfused via an aortic canula in a Langendorff set-up equipped with ECG and MAP electrodes. Global normotherm ischemia was induced by turning off the perfusion for 30 min. After 30 min the heart was reperfused and the total duration of arrhythmia was determined. Furthermore, ECG and surface monophasic action potentials (MAPS) were scored to describe the severity of ischemic damage.

Results:

0.4 µg/ml (2R,3R,4R)-3,4dihydroxy-2-hydroxymethylpyrrolidine reduced the average arrhythmia length following reperfusion from 18.0±5.6 to 0.0±0.0 minutes, (n=7). ECG score was reduced from 2.4±0.2 to 0.7±0.3 (n=7) and MAP score from 2.3±0.3 to 0.9±0.1 (n=7)

Example 3
Evaluation of Cardioprotective Effect in the Anaesthetised Rabbit Model of Myocardial Infarction Induced by Transient Coronary Artery Occlusion Method: Rabbits were anaesthetized and mechanically ventilated with oxygen enriched air. A thoracotomy was performed and an infarct was produced by ligating the left coronary artery for 30 min. After 30 min. the heart was reperfused for 2 hours. The heart was excited and reperfused in Langendorff mode. The coronary artery was reoccluded and the heart was perfused with ink to delineate the area at risk. The heart was removed and cut into 2 mm slices and stained with triphenyl tetrazolium chloride. The area at risk and the infarct size was determined by planimetry.

Results:
10 mg/kg b.i.d. (2R,3R,4R)-3,4dihydroxy-2-hydroxymethylpyrrolidine reduced the infarct size with 45% when compared to untreated rabbits.

Example 4
Reduction of Glycogen Metabolism in Heart Tissue Following Ischemia

Method: The glycogen contents of freeze-clamped heart samples were determined enzymatically as μmol of glycosyl units per gram wet weight after boiling the tissue in 0.4 N KOH and subsequent degradation of glycogen with amyloglycosidase Results:
In hearts subjected to 30 min. of global ischemia the glycogen content was reduced from 15.6±2.8 to 2.6±0.8 (n=4). In the presence of (2R,3R,4R)-3,4dihydroxy-2-hydroxymethylpyrrolidine (0.4 μg/ml) the glycogen content was significantly less reduced, namely from 16.9±1.5 to 6.9±1.1 glycosyl units/g wet weight.

What is claimed is:

1. A method of treating cardiac or cardiovascular disease, wherein said cardiac or cardiovascular disease is arrhythmia comprising administering to subject in need thereof an effective amount of a compound of formula (I)

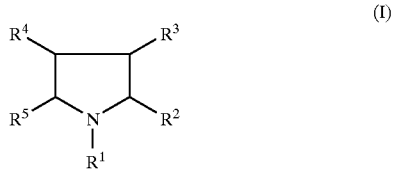

wherein
$R^1$ is hydrogen or acyl, alkenyl, cycloalkyl or alkyl, all of which are optionally substituted with one or more of the following groups: hydroxy, alkoxy, amino, N-alkylamino, N,N-dialkylamino, halogen, cycloalkyl, optionally substituted phenyl or alkoxycarbonyl;
$R^2$ is hydrogen or alkyl;
$R^3$ and $R^4$, which are the same or different, independent of each other, is hydrogen, halogen, hydroxy, mercapto or amino which is optionally substituted with alkyl or aralkyl; and
$R^5$ is alkyl substituted with hydroxy, halogen, amino, N-alkylamino, N,N-dialkylamino or mercapto; or a pharmaceutically acceptable salt or hydrate or prodrug thereof, optical or geometric isomers or tautomeric forms or mixtures thereof.

2. The method according to claim 1, wherein the subject is at risk of contracting arrhythmia.

3. The method according to claim 1, wherein the subject suffers from a disease selected from the group consisting of myocardial infarct, acute coronary syndrome, unstable angina, non-Q-wave cardiac necrosis, Q-wave myocardial infarct and morbidity after stroke.

4. The method according to claim 1, wherein the subject is at risk of contracting a disease selected from the group consisting of myocardial infarct, acute coronary syndrome, unstable angina, non-Q-wave cardiac necrosis, Q-wave myocardial infarct and morbidity after stroke.

5. The method according to claim 1, wherein the subject is a non-diabetic patient.

6. The method according to claim 1, wherein the treatment is in combination with one or more further pharmaceutical agents.

7. The method to claim 6, wherein said further pharmaceutical agent is selected from the group consisting of anti-arrhythmia agents anti-diabetic agents, anti-obesity agents, lipid modulating agents, anti-hypertensive agents and antiosteoporosis agents.

8. The method according to claim 7, wherein the anti-arrhythmia agent is digoxin.

9. The method according to claim 7, wherein the anti-diabetic agent is metformin.

10. The method according to claim 7, wherein the anti-hypertensive agent is an angiotensin converting enzyme inhibitor.

11. The method according to claim 10, wherein the angiotensin converting enzyme inhibitor is selected from the group consisting of captopril, enalapril, fosinopril, lisinopril, quinapril, ramipril and spirapril.

12. The method according to claim 7, wherein the anti-hypertensive agent is an anglotensin II receptor antagonist, e.g. losartan.

13. The method according to claim 7, wherein the anti-hypertensive agent is a non-subtype-selective β-adrenergic antagonist.

14. The method according to claim 13, wherein the non-subtype-selective β-adrenergic antagonist is selected from the group consisting of propranolol, nadolol, timolol and pindolol.

15. The method according to claim 7, wherein the anti-hypertensive agent is a selective $β_1$-adrenergic antagonist.

16. The method according to claim 15, wherein the selective $β_1$-adrenergic antagonist is selected from the group consisting of metoprolol, atenolol, esmolol and acebutolol.

17. A method of increasing survival of transplanted hearts, improving pump function of transplanted hearts, decreasing the frequency of pump failure in transplanted hearts or for reducing the frequency of multi organ failure in connection with heart transplantions, the method comprising administering to a patient with a transplanted heart or about to have a heart transplanted an effective amount of a compound of the general formula (I)

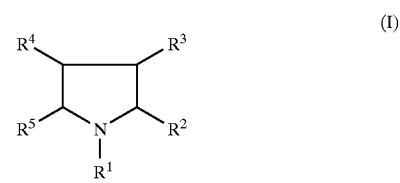

wherein
$R_1$ is hydrogen or acyl, alkenyl cycloalkyl or alkyl, all of which are optionally substituted with one or more of the following groups: hydroxy, alkoxy, amino, N-alkylamino, N,N-dialkylamino, halogen, cycloalkyl, optionally substituted phenyl or alkoxycarbonyl;

$R_2$ is hydrogen or alkyl;

$R^3$ and $R_4$, which are the same or different, independent of each other, is hydrogen, halogen, hydroxy, mercapto or amino which is optionally substituted with alkyl or aralkyl; and $R^5$ is alkyl substituted with hydroxy, halogen, amino, N-alkylamino, N,N-dialkylamino or mercapto;

or a pharmaceutically acceptable salt or hydrate or prodrug thereof, optical or geometric isomers or tautomeric forms mixtures thereof.

18. The method according to claim 1, wherein the compound of formula (I) contains at least two hydroxy groups.

19. The method according to claim 1, wherein the compound of formula (I) contains at least three hydroxy groups.

20. The method according to claim 1, wherein in the compound of formula (I) the two substituents designated the symbols $R_3$ and $R^5$ are situated at the same side of the plane formed by the five membered nitrogen containing ring, and $R_4$ is situated at the opposite side of the plane formed by the five membered nitrogen containing ring.

21. The method according to claim 1, wherein $R^1$ is hydrogen, acyl or alkyl which is optionally substituted with one or more of the following groups: hydroxy, alkoxy, amino, N-alkylamino, N,N-dialkylamino, phenyl or alkoxycarbonyl.

22. The method according to claim 21, wherein $R^1$ is hydrogen or alkyl optionally substituted with one or more of the following groups: hydroxy, alkoxy, amino, N-alkylamino, N,N-dialkylamino, phenyl or alkoxycarbonyl.

23. The method according to claim 21, wherein $R^1$ is $C_{1-6}$-alkyl optionally substituted with one or more of the following groups: hydroxy, alkoxy, amino, N-alkylamino, N,N-dialkylamino, phenyl or alkoxycarbonyl.

24. The method according to claim 21, where in $R^1$ is methyl optionally substituted with one or more of the following groups: hydroxy, alkoxy, amino, N-alkylamino, N,N-dialkylamino, phenyl or alkoxycarbonyl.

25. The method according to claim 21, wherein $R_1$ is hydrogen or alkyl.

26. The method according to claim 21, wherein $R^1$ is $C_{1-6}$-alkyl.

27. The method according to claim 21, wherein $R^1$ is methyl.

28. The method according to claim 21, wherein $R^1$ is hydrogen.

29. The method according to claim 1, wherein $R^1$ is substituted with an optionally substituted phenyl group, optionally substituted with one or more subatituents selected from the group consisting of halogen, hydroxy, alkoxy, trifluoroalkyl and cyano.

30. The method according to claim 1, wherein $R^2$ is $C_{1-6}$-alkyl.

31. The method according to claim 30, wherein $R^2$ is methyl.

32. The method according to claim 1, wherein $R^2$ is hydrogen.

33. The method according to claim 1, wherein $R^3$ is hydrogen, hydroxy, halogen or amino.

34. The method according to claim 33, wherein $R^3$ is hydroxy, halogen or amino.

35. The method according to claim 33, wherein $R^3$ is hydroxy or halogen.

36. The method according to claim 33, wherein $R^3$ is fluoro.

37. The method according to claim 33, wherein $R^3$ is hydroxy.

38. The method according to claim 1, wherein $R^4$ is hydrogen, hydroxy, halogen or amino.

39. The method according to claim 38, wherein $R^4$ is hydroxy, halogen or amino.

40. The method according to claim 38, wherein $R^4$ is hydroxy or halogen.

41. The method according to claim 38, wherein $R^4$ is fluoro.

42. The method according to claim 38, wherein $R^4$ is hydroxy.

43. The method according to claim 1, wherein $R^5$ is hydroxyalkyl.

44. The method according to claim 43, wherein $R^5$ is $C_{1-6}$-hydroxyalkyl.

45. The method according to claim 43, wherein $R^5$ is hydroxymethyl, hydroxyethyl or hydroxypropyl.

46. The method according to claim 43, wherein $R^5$ is hydroxymethyl.

47. The method according to claim 1, wherein $R^5$ is benzyloxymethyl.

48. The method according to claim 1, wherein the compound of the general formula (I) is selected from the following:

3,4-dihydroxy-2-hydroxymethylpyrrolidine, 3-4-dihydroxy-2-hydroxymethyl-1-methylpyrrolidine, 1-cyclopropylmethyl-3,4-dihydroxy-2-hydroxymethylpyrrolidine, 3,4-dihydroxy-2-hydroxymethyl-1-propylpyrrolidine, 1-butyl-3,4-dihydroxy-2-hydroxymethylpyrrolidine, 3,4-dihydroxy-2-hydroxymethyl-1-(2,2,2-trifluoroethyl)-pyrrolidine, 1-benzyl-3,4-dihydroxyy-2-hydroxymethylpyrrolidine, 3,4-dihydroxy-2-hydroxymethyl-1-(2-hydroxyethyl)pyrrolidine, 3,4-dihydroxy-2-hydroxymethyl-1-(1,3-dihydroxyprop-2-yl)pyrrolidine, 3,4-dihydroxy-2-hydroxymethyl-1-(2,3-dihydroxyprop-1-yl)pyrrolidine, and 1-(2-aminoethyl)-3,4-dihydroxy-2-hydroxymethylpyrrolidine, or any of the optical isomers thereof.

49. The method according to claim 1, wherein the compound of the general formula (I) is selected from the following:

(2R,3R,4R)-3,4dihydroxy-2-hydroxymethylpyrrolidine, (2R,3R,4R)-3,4-dihydroxy-2-hydroxymethyl-1-methylpyrrolidine, (2R,3R,4R)-1-cyclopropylmethyl-3,4-dihydroxy-2-hydroxymethylpyrrolidine, (2R,3R,4R)-3,4-dihydroxy-2-hydroxymethyl-1-propylpyrrolidine, (2R,3R,4R)-1-butyl-3,4dihydroxy-2-hydroxymethylpyrrolidine, (2R,3R,4R)-3,4-dihydroxy-2-hydroxymethyl-1-(2,2,2-trifluoroethyl)pyrrolidine, (2R,3R,4R)-1-benzyl-3,4-dihydroxy-2-hydroxymethylpyrrolidine, (2R,3R,4R)-3,4-dihydroxy-2-hydroxymethyl-1-(2-hydroxyethyl)pyrrolidine, (2R,3R,4R)-3,4-dihydroxy-2-hydroxymethyl-1-(2,3-dihydroxyprop-1-yl)pyrrolidine, (2R,3R,4R)-3,4-dihydroxy-2-hydroxymethyl-1-(1,3-dihydroxyprop-2-yl)pyrrolidine, (2R,3R,4R)-1-(2-aminoethyl)-3,4-dihydroxy-2-hydroxymethylpyrrolidine, (2S,3S,4S)-3,4-dihydroxy-2-hydroxymethylpyrrolidine, (2S,3S,4S)-3,4-dihydroxy-2-hydroxymethyl-1-methylpyrrolidine, (2S,3S,4S)-1-cyclopropylmethyl-3,4-dihydroxy-2-hydroxymethylpyrrolidine, (2S,3S,4S)-3,4-dihydroxy-2-hydroxymethyl-1-propylpyrrolidine, (2S,3S,4S)-1-butyl-3,4-dihydroxy-2-hydroxymethylpyrrolidine, (2S,3S,4S)-3,4-dihydroxy-2-hydroxymethyl-1-(2,2,2-trifluoroethyl)pyrrolidine, (2S,3S,4S)-1-benzyl-3,4-dihydroxy-2-hydroxymethylpyrrolidine, (2S,3S,4S)-3,4-dihydroxy-2-hydroxymethyl-1-(2-hydroxyethyl)pyrrolidine, (2S,3S,4S)-3,4-dihydroxy-2-hydroxymethyl-1-(2,3-dihydroxyprop-1-yl)pyrrolidine, (2S,3S,4S)-3,4-dihydroxy-2-hydroxymethyl-1-(1,3-dihydroxyprop-2-yl)-pyrrolidine, and (2S,3S,4S)-1-(2-aminoethyl)-3,4-dihydroxy-2-hydroxymethyl-pyrrolidine.

50. The method according to claim 17, wherein the compound of the general formula (I) is selected from the following:

3,4-dihydroxy-2-hydroxymethylpyrrolidine, 3-4-dihydroxy-2-hydroxymethyl-1-methylpyrrolidine, 1-cyclopropylmethyl-3,4-dihydroxy-2-hydroxymethylpyrrolidine, 3,4-dihydroxy-2-hydroxymethyl-1-propylpyrrolidine, 1-butyl-3,4-dihydroxy-2-hydroxymethylpyrrolidine, 3,4-dihydroxy-2-hydroxymethyl-1-(2,2,2-trifluoroethyl)-pyrrolidine, 1-benzyl-3,4-dihydroxyy-2-hydroxymethylpyrrolidine, 3,4-dihydroxy-2-hydroxymethyl-1-(2-hydroxyethyl)pyrrolidine, 3,4-dihydroxy-2-hydroxymethyl-1-(1,3-dihydroxyprop-2-yl)pyrrolidine, 3,4-dihydroxy-2-hydroxymethyl-1-(2,3-dihydroxyprop-1-yl)pyrrolidine, and 1-(2-aminoethyl)-3,4-dihydroxy-2-hydroxymethylpyrrolidine, or any of the optical isomers thereof.

51. The method according to claim 17, wherein the compound of the general formula (I) is selected from the following:

(2R,3R,4R)-3,4dihydroxy-2-hydroxymethylpyrrolidine, (2R,3R,4R)-3,4-dihydroxy-2-hydroxymethyl-1-methylpyrrolidine, (2R,3R,4R)-1-cyclopropylmethyl-3,4-dihydroxy-2-hydroxymethylpyrrolidine, (2R,3R,4R)-3,4-dihydroxy-2-hydroxymethyl-1-propylpyrrolidine, (2R,3R,4R)-1-butyl-3,4dihydroxy-2-hydroxymethylpyrrolidine, (2R,3R,4R)-3,4-dihydroxy-2-hydroxymethyl-1-(2,2,2-trifluoroethyl)pyrrolidine, (2R,3R,4R)-1-benzyl-3,4-dihydroxy-2-hydroxymethylpyrrolidine, (2R,3R,4R)-3,4-dihydroxy-2-hydroxymethyl-1-(2-hydroxyethyl)pyrrolidine, (2R,3R,4R)-3,4-dihydroxy-2-hydroxymethyl-1-(2,3-dihydroxyprop-1-yl)pyrrolidine, (2R,3R,4R)-3,4-dihydroxy-2-hydroxymethyl-1-(1,3-dihydroxyprop-2-yl)pyrrolidine, (2R,3R,4R)-1-(2-aminoethyl)-3,4-dihydroxy-2-hydroxymethylpyrrolidine, (2S,3S,4S)-3,4-dihydroxy-2-hydroxymethylpyrrolidine, (2S,3S,4S)-3,4-dihydroxy-2-hydroxymethyl-1-methylpyrrolidine, (2S,3S,4S)-1-cyclopropylmethyl-3,4-dihydroxy-2-hydroxymethylpyrrolidine, (2S,3S,4S)-3,4-dihydroxy-2-hydroxymethyl-1-propylpyrrolidine, (2S,3S,4S)-1-butyl-3,4-dihydroxy-2-hydroxymethylpyrrolidine, (2S,3S,4S)-3,4-dihydroxy-2-hydroxymethyl-1-(2,2,2-trifluoroethyl)pyrrolidine, (2S,3S,4S)-1-benzyl-3,4-dihydroxy-2-hydroxymethylpyrrolidine, (2S,3S,4S)-3,4-dihydroxy-2-hydroxymethyl-1-(2-hydroxyethyl)pyrrolidine, (2S,3S,4S)-3,4-dihydroxy-2-hydroxymethyl-1-(2,3-dihydroxyprop-1-yl)pyrrolidine, (2S,3S,4S)-3,4-dihydroxy-2-hydroxymethyl-1-(1,3-dihydroxyprop-2-yl)-pyrrolidine, and (2S,3S,4S)-1-(2-aminoethyl)-3,4-dihydroxy-2-hydroxymethyl-pyrrolidine.

\* \* \* \* \*